(12) United States Patent
Zhang et al.

(10) Patent No.: US 12,410,453 B2
(45) Date of Patent: Sep. 9, 2025

(54) MILBEMYCIN STRAIN WITH HIGH-YIELD AND ITS APPLICATION

(71) Applicant: Hubei Honch Pharmaceutical Co., Ltd, Hubei (CN)

(72) Inventors: Renwen Zhang, Hubei (CN); Wenkai Zhang, Hubei (CN); Wei Zheng, Hubei (CN); Wenke Li, Hubei (CN); Jianye Gan, Hubei (CN); Hua Dong, Hubei (CN); Liyun Ke, Hubei (CN); Jiaxin Zhang, Hubei (CN); Li Tian, Hubei (CN); Xueling Jiang, Hubei (CN)

(73) Assignee: Hubei Honch Pharmaceutical Co., Ltd, Huanggang (CN)

( * ) Notice: Subject to any disclaimer, the term of this patent is extended or adjusted under 35 U.S.C. 154(b) by 0 days.

(21) Appl. No.: 18/400,012

(22) Filed: Dec. 29, 2023

(65) Prior Publication Data

US 2025/0122544 A1   Apr. 17, 2025

(30) Foreign Application Priority Data

Oct. 12, 2023   (CN) .................. 202311320097.X

(51) Int. Cl.
| C12P 17/18 | (2006.01) |
| C12N 1/20 | (2006.01) |
| C12R 1/55 | (2006.01) |

(52) U.S. Cl.
CPC ............ *C12P 17/181* (2013.01); *C12N 1/205* (2021.05); *C12R 2001/55* (2021.05)

(58) Field of Classification Search
CPC .... C12P 17/181; C12N 1/205; C12R 2001/55
See application file for complete search history.

(56) References Cited

FOREIGN PATENT DOCUMENTS

| CN | 87108339 A | | 7/1988 |
| CN | 101037442 A | * | 9/2007 |
| CN | 101100651 A | | 1/2008 |
| CN | 105906650 A | | 8/2016 |
| CN | 106148216 A | | 11/2016 |
| CN | 109207536 A | | 1/2019 |
| KR | 20190031865 A | | 3/2019 |

OTHER PUBLICATIONS

CN101037442A, Espacenet Machine Translation, pp. 1-5 (Year: 2007).*
Notice of Allowance of counterpart Chinese Patent Application No. 202311320097.X issued on Jun. 6, 2024.
Zhenbin Lyu et al., Preliminary Study on Milbemycin Biosynthesis of Streptomyces milbemycinicus DSM41911, Journal of Microbiology, Dec. 2016, pp. 24-28, vol. 36, No. 6.
Shigetoshi Okada et al., Scale-up Production of Milbemycin by *Streptomyces hygroscopicus* subsp. aureolacrimosus with Control of Internal Pressure, Temperature, Aeration and Agitation, Journal of Chemical Technology and Biotechnology, 1997, pp. 179-187, vol. 70.

* cited by examiner

*Primary Examiner* — Thea D'Ambrosio
*Assistant Examiner* — Claudia Espinosa

(57) ABSTRACT

A strain for high-yield production of milbemycin and use thereof is disclosed. In the present invention, an original strain MI-W1-2017001 is subjected to mutation breeding by an atmospheric and room temperature plasma mutation method to obtain a high-yield strain HZMRYB-5. The fermentation level of the strain is improved by about 70% compared with the original strain, and the fermentation level is further improved by about 35% through optimization of a fermentation process and a formulation, so that the fermentation cost of the product is further reduced, and requirements for the industrial fermentation level are met. On the basis of optimizing the fermentation process, the ratio of A3 and A4 in a fermentation liquid is nearly 3:7 through mixed fermentation of the strain MI-W1-2017001 and the strain HZMRYB-5, so that market demands are greatly met, the process steps of separation, purification and then mixing are reduced.

5 Claims, No Drawings

MILBEMYCIN STRAIN WITH HIGH-YIELD AND ITS APPLICATION

CROSS REFERENCE TO RELATED APPLICATION

This application claims priority of Chinese Application No. 202311320097.X filed on Oct. 12, 2023 and entitled "Milbemycin strain with high yield and its application", the contents of which are incorporated herein by reference in their entirety.

FIELD OF TECHNOLOGY

The present invention belongs to the technical field of microbial fermentation, and specifically relates to a strain for high-yield production of milbemycin and use thereof.

BACKGROUND

Milbemycin oxime is a macrolide drug for resisting in vivo or in vitro parasites, which is an oxime derivative of milbemycin A3 and milbemycin A4. The milbemycin oxime has a broad-spectrum anti-parasitic effect, which has a good repellent killing effect on in vivo or in vitro parasites, especially nematodes and arthropods. The milbemycin oxime is one of main anti-parasitic products for animals in Japan and European and American countries.

Milbemycin is a secondary metabolite obtained by deep liquid fermentation of *Streptomyces milbemycinicus*. The milbemycin is a 16-membered macrolide antibiotic with strong biological activities, such as insecticidal activity, acaricidal activity, pest repellent activity and anti-tumor activity. However, the milbemycin generally has the technical problems of a complicated production process, a low fermentation level and the like. In addition, dosage forms of milbemycin strictly require the ratio of A3 and A4 in a milbemycin mixture (A3:A4=3:7). Thus, milbemycin production technologies are only grasped by few enterprises at present, and it is difficult for conventional strains to meet the requirement. Therefore, it is necessary to screen strains with appropriate ratios or to screen strains with high proportions of A3 and high proportions of A4 for fermentation, separation, purification and then mixing so as to meet market demands.

SUMMARY

The present application takes a strain of *Streptomyces hygroscopicus* var. *aureolacrimosus* MI-W1-2017001 as an original strain, the original strain is subjected to mutation breeding by an atmospheric and room temperature plasma (ARTP) mutation, and finally, a strain HZMRYB-5 for high-yield production of milbemycin is obtained. The ratio of milbemycin A3 and milbemycin A4 in the fermentation broth of strain HZMRYB-5 is greatly different from that of the original strain, and the titer of milbemycin is further improved by optimizing a fermentation process.

In a first technical scheme, the present invention provides a strain of *Streptomyces hygroscopicus* var. *aureolacrimosus*, specifically *Streptomyces hygroscopicus* var. *aureolacrimosus* HZMRYB-5. The strain has been deposited in China Center for Type Culture Collection (CCTCC) on Aug. 25, 2023 in Wuhan University, Wuhan, China, with a zip code of 430072 and a deposit number of CCTCC: M 20231540. The strain was deposited at CCTCC under the Budapest Treaty and will be made available to the public upon issuance of a patent.

Mutation conditions: the mutation time is: 10-160 s, the radio-frequency power is 120 W; the distance between a plasma emission source and a sampling platform is 2 mm; and the gas flow rate is 10 L/min. Further, the optimum mutation time is 100 s.

In a second technical scheme, the present invention provides use of the strain HZMRYB-5 as mentioned in the first scheme, especially in production of milbemycin. The strain HZMRYB-5 is taken as a fermentation strain in a method for producing milbemycin by fermentation.

In a third technical scheme, the present invention provides a method for producing milbemycin by fermentation. The method specifically includes the following steps:

inoculating a seed liquid of a strain HZMRYB-5 into a fermentation culture medium at an inoculation amount of 5-20%, where the culture temperature is 28.0-30.0° C. in the whole process; the tank pressure is 0.02-0.06 Mpa; ventilation is controlled at 0.2-1.0 vvm at 0-24 h, gradually increased to 1.0-1.8 vvm, and then gradually decreased to 1.0-1.2 vvm before completion of fermentation; the rotation speed is gradually increased to 250-500 rpm at 0-48 h, and gradually decreased to 100-200 rpm in a later stage of fermentation; the pH is natural; the dissolved oxygen (DO) value is controlled to be equal to or greater than 50%; and the fermentation period is 300-400 h.

Further, the ventilation is gradually decreased to 1.0-1.2 vvm at 12-144 h before completion of fermentation.

Further, the rotation speed is gradually decreased to 100-200 rpm at 20-120 h before completion of fermentation.

The fermentation volume is maintained. A small amount of sterile water is supplemented every day to maintain a fermentation liquid at a constant volume.

Further, the fermentation culture medium includes: 10-30% of sucrose, 0.5-3% of skim milk powder, 2-4% of soybean meal powder, 1-4% of cottonseed cake meal, 0.1-0.5% of potassium nitrate, 0.1-0.5% of dipotassium hydrogen phosphate, 0.1-1.0% of zeolite powder, 0.001-0.01% of sodium molybdate, 0.01-0.1% of magnesium sulfate heptahydrate, 0.01-0.05% of ferrous sulfate, 0.01-0.1% of sodium acetate, 0.1-1% of methyl oleate, 0.1-1% of liquid paraffin and the balance of water, and has a pH value of 7.2.

Preferably, the fermentation culture medium includes: 20% of sucrose, 2% of skim milk powder, 2% of soybean meal powder, 2% of cottonseed cake meal, 0.1% of potassium nitrate, 0.2% of dipotassium hydrogen phosphate, 0.4% of zeolite powder, 0.005% of sodium molybdate, 0.05% of magnesium sulfate heptahydrate, 0.01% of ferrous sulfate, 0.04% of sodium acetate, 0.1% of methyl oleate, 0.5% of liquid paraffin and the balance of water, and has a pH value of 7.2.

Further, when the total sugar content is about 5.0-8.0%, a supplement culture medium is supplemented in 1-3 times every day according to 1-4% of the volume of the fermentation liquid.

Further, the supplement culture medium includes: all materials in a formulation of the fermentation culture medium with a double concentration.

Further, the seed liquid is obtained by mixed culture of a strain MI-W1-2017001 and a strain HZMRYB-5, where during preparation of the seed liquid, the strain MI-W1-2017001 and the strain HZMRYB-5 are inoculated at a ratio of 1:(0.5-3); and preferably, the strain MI-W1-2017001 and the strain HZMRYB-5 are inoculated at a ratio of 1:2.

The strain MI-W1-2017001 is specifically *Streptomyces hygroscopicus* var. *aureolacrimosus* MI-W1-2017001, and the strain has been stored in China Center for Type Culture Collection on Mar. 29, 2021 in Wuhan University, Wuhan, China, with a zip code of 430072 and a deposit number of CCTCC NO: M 2021292. The strain was deposited at CCTCC under the Budapest Treaty and will be made available to the public upon issuance of a patent.

Beneficial effects are as follows.

In the present invention, an original strain MI-W1-2017001 is subjected to mutation breeding by an atmospheric and room temperature plasma (ARTP) mutation, and finally, a strain HZMRYB-5 for high-yield production of milbemycin is screened. The fermentation yield of the strain is improved by about 70% compared with the original strain, and the fermentation level is further improved by about 35% through optimization of a fermentation process and a formulation, so that the fermentation cost of the product is further reduced, and requirements for the industrial fermentation level are met.

The ratio of A3 and A4 in a fermentation liquid is improved. On the basis of optimizing the fermentation process, the ratio of A3 and A4 in a fermentation liquid is nearly 3:7 through mixed fermentation of the strain MI-W1-2017001 and the strain HZMRYB-5, so that market demands are greatly met, the process steps of separation, purification and then mixing are reduced, and a good application prospect is achieved.

DESCRIPTION OF THE EMBODIMENTS

The present invention is described below through specific embodiments. Unless otherwise specified, all technical means used in the present invention are methods known to persons skilled in the art. In addition, the embodiments shall be understood to be illustrative and are not intended to limit the scope of the present invention, and the essence and scope of the present invention are limited only by the claims. For persons skilled in the art, any alterations or modifications of material components and dosages in the embodiments made without deviating from the essence and scope of the present invention shall also fall within the scope of protection of the present invention.

A method for testing milbemycin in a fermentation liquid in the present invention is as follows.

(1) Treatment of a Milbemycin Fermentation Liquid

Sample treatment: 3 mL of a fermentation liquid is added into 12 mL of methanol and then uniformly mixed by a mixer, a mixed liquid is subjected to ultrasonic extraction for 2 h and centrifuged at 8,000 r/min for 10 min, and then a centrifuged liquid is collected, filtered with a microporous membrane and tested on a machine.

(2) Chromatographic Conditions are as Follows: Chromatographic Column: 250 mm×4.6 mm; 5 µm C18;
  detector: UV detector; detection wavelength: 240 nm;
  sample volume: 20 µl; flow rate: 1.0 mL/min;
  column temperature: 35° C.;
  mobile phases: A: acetonitrile, B: water.

| Time (min) | A (acetonitrile) | B (water) |
|---|---|---|
| 0 | 70 | 30 |
| 25 | 70 | 30 |
| 35 | 85 | 15 |
| 50 | 85 | 15 |
| 55 | 70 | 30 |
| 60 | 70 | 30 |

(3) Preparation of a Control Product Solution:

About 10 mg of a milbemycin working control product is accurately weighed and added into a 50 mL volumetric flask, and methanol is added for dissolving and diluting the control product to a certain scale and then uniformly shaken to obtain the control product solution.

(4) Calculation of the Concentration of Milbemycin A3 or A4 Per Unit Volume

A calculation formula (external standard method) is as follows:

$$\mu g/ml = \frac{A_{sample}}{A_{control;}} \times C_{control} \times F \times \text{dilution ratio}$$

in the formula, $A_{sample}$ refers to the peak area of milbemycin A3 or A4 in a chromatogram of a test product solution;

$A_{control}$ refers to the peak area of milbemycin A3 or A4 in a chromatogram of a control product solution;

$C_{control}$ refers to the concentration of milbemycin in a milbemycin control product, µg/mL;

F refers to the content of milbemycin A3 or A4 in the milbemycin control product.

Note: In the control product used in the present invention, the content of milbemycin A3 is 18.43%, and the content of milbemycin A4 is 80.71%.

The sum of the concentrations of milbemycin A3 and milbemycin A4 per unit volume=volume concentration of milbemycin A3+volume concentration of milbemycin A4. The "titer" in the present invention refers to the total concentration of A3 and A4.

The present invention is further illustrated below through specific embodiments.

Example 1 ARTP (Atmospheric and Room Temperature Plasma) Mutation Breeding

One. Conditions of ARTP Mutation

1. Culture Media Involved in Mutation and Screening Processes

A solid (slope) culture medium includes: 0.4% of sucrose, 0.3% of skim milk powder, 0.2% of yeast powder, 0.5% of malt extract powder, 0.05% of magnesium sulfate, 0.001% of copper sulfate, 0.001% of cobalt sulfate, 2% of agar and the balance of water, and has a pH value of 7.2.

A seed culture medium includes: 1% of sucrose, 0.5% of skim milk powder, 0.5% of yeast extract powder, 0.5% of peptone, 0.2% of dipotassium hydrogen phosphate and the balance of water, and has a pH value of 7.2.

A fermentation culture medium includes: 20% of sucrose, 2% of skim milk powder, 2% of soybean meal powder, 2% of cottonseed cake meal, 0.1% of potassium nitrate, 0.2% of dipotassium hydrogen phosphate, 0.4% of zeolite powder, 0.005% of sodium molybdate, 0.05% of magnesium sulfate heptahydrate, 0.01% of ferrous sulfate and 0.04% of sodium acetate, and has a pH value of 7.2.

2. Preparation of a Bacterial Suspension

A milbemycin producing strain MI-W1-2017001 stored in a laboratory was inoculated into a slope culture medium and cultured at 28° C. for about 15 days. When gray and thick spores on a front surface and a light brown pigment on a back surface were observed, the spores were eluted with sterile water, added into a conical flask with glass beads, shaken on a shaker for 10 min and then filtered to obtain a spore suspension. The spore suspension was diluted to a concentration of $10^6$ cfu/mL for later use.

The strain MI-W1-2017001 is specifically *Streptomyces hygroscopicus* var. *aureolacrimosus* MI-W1-2017001, and the strain has been stored in China Center for Type Culture Collection on Mar. 29, 2021 in Wuhan University, Wuhan, China, with a zip code of 430072 and a deposit number of CCTCC NO: M 2021292.

3. Mutation Treatment

Mutation method: A fatality curve was drawn according to a mutation fatality rate, and the bacterial suspension was subjected to mutation by an ARTP (atmospheric and room temperature plasma) mutation technology, where the mutation time was: 10 s, 20 s, 40 s, 60 s, 80 s, 100 s, 120 s, 140 s and 160 s, and mutation conditions were set as follows: the radio-frequency power was 120 W; the distance between a plasma emission source and a sampling platform was 2 mm; and the gas flow rate was 10 L/min.

After the mutation treatment for different times, the bacterial suspension was diluted to $10^{-3}$ and $10^{-4}$ with sterile water, 100 µL of the bacterial suspension was taken and coated on the solid culture medium for anaerobic culture at 28° C. for 15 days, the number of bacterial colonies on a plate was counted, and the fatality rate at different mutation times was determined, as shown in Table 1 below.

TABLE 1

Fatality rate of a strain MI-W1-2017001 at different mutation times

| | Mutation time | | | | | | | |
|---|---|---|---|---|---|---|---|---|
| | 10 s | 20 s | 40 s | 60 s | 80 s | 100s | 120 s | 140 s | 160 s |
| Fatality rate (%) | 0 | 5.13 | 10.42 | 40.20 | 65.32 | 83.74 | 93.53 | 100 | 100 |

Literature shows that the positive mutation rate is the highest when the mortality rate of ARTP mutation breeding is about 85%. Thus, the mortality rate is 83.74% when the optimal mutation time is determined to be 100 s.

Two. ARTP Mutation (Resistance Screening)

1. Tolerance to Milbemycin of an Original Strain

An original strain MI-W1-2017001 was inoculated into a slope culture medium and cultured at 28° C. for about 15 days. When gray and thick spores on a front surface and a light brown pigment on a back surface were observed, the spores were eluted with sterile water, added into a conical flask with glass beads, shaken on a shaker for 10 min and then filtered to obtain a spore suspension. The spore suspension was diluted to a concentration of $10^6$ cfu/mL for later use.

The bacterial suspension was diluted and coated on solid culture media containing 0.4%, 0.6%, 0.8%, 1.0%, 1.2%, 1.4% and 1.6% of milbemycin (the ratio of A3 and A4 was 1:1), respectively, and growth conditions of the original strain were observed. Results are shown in Table 2 below.

TABLE 2

Results of the tolerance to milbemycin of an original strain

| | Concentration of milbemycin % | | | | | | |
|---|---|---|---|---|---|---|---|
| | 0.4 | 0.6 | 0.8 | 1.0 | 1.2 | 1.4 | 1.6 |
| Growth situation | Grow normally | Slightly inhibited | Obviously inhibited | Not grow | Not grow | Not grow | Not grow |

As can be seen from the results, the growth of the original strain is obviously inhibited in the culture medium containing 0.8% of milbemycin, and the growth is completely inhibited in the culture medium containing 1.0% of milbemycin.

2. Mutation of a Bacterial Suspension by an ARTP (Atmospheric and Room Temperature Plasma) Mutation Preparation of a bacterial suspension: An original strain MI-W1-2017001 was inoculated into a slope culture medium and cultured at 28° C. for about 15 days. When gray and thick spores on a front surface and a light brown pigment on a back surface were observed, the spores were eluted with sterile water, added into a conical flask with glass beads, shaken on a shaker for 10 min and then filtered to obtain a spore suspension. The spore suspension was diluted to a concentration of $10^6$ cfu/mL for later use.

Mutation conditions were set as follows: The bacterial suspension was subjected to mutation by an ARTP (atmospheric and room temperature plasma) mutation technology; the radio-frequency power was 120 W; the distance between a plasma emission source and a sampling platform was 2 mm; the gas flow rate was 10 L/min; and the mutation time was 100 s.

3. Screening of Mutant Strains (1) Milbemycin Tolerance Screening

The mutated bacterial suspension was diluted and coated on solid culture media containing 0.4%, 0.6%, 0.8%, 1.0%, 1.2%, 1.4% and 1.6% of milbemycin (the ratio of A3 and A4 was 1:1), respectively, and growth conditions of mutant strains were observed. Bacterial colonies capable of growing normally in the culture media containing 0.8% or more of milbemycin were selected.

(2) Preliminary Screening in a Shake Flask

Bacterial colonies capable of growing normally in the culture media containing 0.8% or more of milbemycin were selected and subjected to passage culture on normal solid small slopes for 15 days. The small slopes with normal growth were collected to carry out preliminary screening by a shake flask fermentation experiment.

Through resistance screening in step (1), a total of 62 potential mutant strains were obtained. The 62 strains were subjected to passage culture on small slopes of test tubes. 1 $cm^2$ bacterial moss was scraped from the slope with good growth, inoculated into a sterile fermentation shake flask on a shaker at a rotation speed of 250 rpm, and then cultured at a temperature of 29° C. for a period of 13 days. During normal growth, the color of a fermentation liquid was gradually changed from gray to green and then changed from green to black. The color changed into black indicates normal metabolism of the strain. Meanwhile, mycelia were thick, reticular, deeply stained and free of hybrid bacteria in microscopic examination. Results of the titer of milbemycin in fermentation liquids of 62 strains are shown in Table 3 below.

TABLE 3

Preliminary results of mutant strains in a shake flask

| Strain number | Titer μg/mL | Increase range % | A3:A4 |
|---|---|---|---|
| MI-W1-2017001 | 3008.24 | 0.00 | 1:0.78 |
| HZMRYB-1 | 2126.32 | −29.32 | 1:0.83 |
| HZMRYB-2 | 4206.92 | 39.85 | 1:1.24 |
| HZMRYB-3 | 2058.28 | −31.58 | 1:0.66 |
| HZMRYB-4 | 3160.50 | 5.06 | 1:0.92 |
| HZMRYB-5 | 5120.47 | 70.21 | 1:5.67 |
| HZMRYB-6 | 1246.28 | −58.57 | 1:0.65 |
| HZMRYB-7 | 1478.42 | −50.85 | 1:0.87 |
| HZMRYB-8 | 2460.45 | −18.21 | 1:0.63 |
| HZMRYB-9 | 2911.98 | −3.20 | 1:0.92 |
| HZMRYB-10 | 2208.62 | −26.58 | 1:0.79 |
| HZMRYB-11 | 4072.30 | 35.37 | 1:1.32 |
| HZMRYB-12 | 1431.11 | −52.43 | 1:1.52 |
| HZMRYB-13 | 4608.16 | 53.18 | 1:2.65 |
| HZMRYB-14 | 2647.25 | −12.00 | 1:0.77 |
| HZMRYB-15 | 1206.40 | −59.90 | 1:0.93 |
| HZMRYB-16 | 3010.49 | 0.07 | 1:0.98 |
| HZMRYB-17 | 2381.72 | −20.83 | 1:0.76 |
| HZMRYB-18 | 3021.00 | 0.42 | 1:0.90 |
| HZMRYB-19 | 3011.16 | 0.10 | 1:0.67 |
| HZMRYB-20 | 3702.09 | 23.06 | 1:1.88 |
| HZMRYB-21 | 2022.48 | −32.77 | 1:1.52 |
| HZMRYB-22 | 3070.37 | 2.07 | 1:0.88 |
| HZMRYB-23 | 1146.58 | −61.89 | 1:2.83 |
| HZMRYB-24 | 4310.85 | 43.30 | 1:3.24 |
| HZMRYB-25 | 2999.66 | −0.29 | 1:0.76 |
| HZMRYB-26 | 1220.48 | −59.43 | 1:1.28 |
| HZMRYB-27 | 2263.61 | −24.75 | 1:0.67 |
| HZMRYB-28 | 3022.42 | 0.47 | 1:0.74 |
| HZMRYB-29 | 3172.90 | 5.47 | 1:0.78 |
| HZMRYB-30 | 1280.87 | −57.42 | 1:1.83 |
| HZMRYB-31 | 3839.07 | 27.62 | 1:1.29 |
| HZMRYB-32 | 3032.08 | 0.79 | 1:0.58 |
| HZMRYB-33 | 4956.61 | 64.77 | 1:3.90 |
| HZMRYB-34 | 2191.18 | −27.16 | 1:1.47 |
| HZMRYB-35 | 3093.55 | 2.84 | 1:0.69 |
| HZMRYB-36 | 4189.24 | 39.26 | 1:1.78 |
| HZMRYB-37 | 3206.01 | 6.57 | 1:0.72 |
| HZMRYB-38 | 1096.73 | −63.54 | 1:1.48 |
| HZMRYB-39 | 1301.01 | −56.75 | 1:0.98 |
| HZMRYB-40 | 3165.20 | 5.22 | 1:0.82 |
| HZMRYB-41 | 3793.55 | 26.11 | 1:1.32 |
| HZMRYB-42 | 2767.58 | −8.00 | 1:0.83 |
| HZMRYB-43 | 1956.21 | −34.97 | 1:2.33 |
| HZMRYB-44 | 2622.41 | −12.83 | 1:0.58 |
| HZMRYB-45 | 3065.98 | 1.92 | 1:0.96 |
| HZMRYB-46 | 3842.52 | 27.73 | 1:1.52 |
| HZMRYB-47 | 3110.83 | 3.41 | 1:0.79 |
| HZMRYB-48 | 2327.42 | −22.63 | 1:1.67 |
| HZMRYB-49 | 1360.15 | −54.79 | 1:3.75 |
| HZMRYB-50 | 4725.20 | 57.08 | 1:1.48 |
| HZMRYB-51 | 2679.02 | −10.94 | 1:0.88 |
| HZMRYB-52 | 1893.62 | −37.05 | 1:3.28 |
| HZMRYB-53 | 3046.52 | 1.27 | 1:0.89 |
| HZMRYB-54 | 3029.60 | 0.71 | 1:0.92 |
| HZMRYB-55 | 4239.51 | 40.93 | 1:3.47 |
| HZMRYB-56 | 3020.24 | 0.40 | 1:0.88 |
| HZMRYB-57 | 1109.89 | −63.11 | 1:3.66 |
| HZMRYB-58 | 1316.62 | −56.23 | 1:2.54 |
| HZMRYB-59 | 3869.25 | 28.62 | 1:1.92 |
| HZMRYB-60 | 2435.47 | −19.04 | 1:0.79 |
| HZMRYB-61 | 1721.47 | −42.77 | 1:1.89 |
| HZMRYB-62 | 3405.92 | 13.22 | 1:0.92 |

As can be seen from the above results, 14 positive mutant strains are obtained through preliminary screening of the mutant strains in a shake flask, where 3 high-yield mutant strains (including HZMRYB-5, HZMRYB-13 and HZMRYB-33) have obviously better fermentation titer than the original strain, and the fermentation titer of the 3 mutant strains is improved by 50% or above compared with the original strain. Meanwhile, the ratio of A3 and A4 in these strains is also obviously changed.

(3) Secondary Screening by Fermentation

The 3 high-yield strains obtained from the preliminary screening were subjected to passage culture on solid culture media for 15 days for later use. Small slopes with normal growth were collected to carry out preliminary screening by a shake flask fermentation experiment. 1 $cm^2$ seeds on the slopes were scraped off with sterile inoculation needles, inoculated into seed culture media and cultured at 250 rpm at 29° C. for about 48 h to obtain thick seed liquids. When a large amount of mycelia in a dense reticular shape were observed under a microscope, the seed liquids were transferred into fermentation culture media.

The seed liquids were inoculated into fermentation culture medium flasks at a liquid loading amount of 30 mL/250 mL, an inoculation amount of 10% and a shaker rotation speed of 250 rpm, and then cultured at a temperature of 29° C. for a period of 13 days. During normal growth, the color of a fermentation liquid was gradually changed from gray to green and then changed from green to black. The color changed into black indicates normal metabolism of the strain. Meanwhile, mycelia were thick, reticular, deeply stained and free of hybrid bacteria in microscopic examination. Results of the titer of milbemycin in fermentation liquids of 3 strains are shown in Table 4 below.

TABLE 4

Secondary screening results of dominant strains

| | Strain number | | | | | |
|---|---|---|---|---|---|---|
| | HZMRYB-5 | A3:A4 | HZMRYB-13 | A3:A4 | HZMRYB-33 | A3:A4 |
| Titer μg/mL | 5225.40 | 1:5.43 | 4621.12 | 1:2.49 | 4924.30 | 1:3.82 |
| | 5195.25 | 1:5.55 | 4638.52 | 1:2.44 | 4837.38 | 1:3.77 |
| | 5202.38 | 1:5.38 | 4625.10 | 1:2.51 | 4822.47 | 1:3.83 |

As can be seen from the secondary screening results, the secondary screening results and the preliminary screening results have no obvious differences, and the titer of the strain HZMRYB-5/HZMRYB-13/HZMRYB-33 is greatly improved compared with that of the original strain MI-W1-2017001. Meanwhile, the proportion of A4 in the fermentation liquids of the three strains is significantly improved, which is greatly different from that of the original strain, indicating that the 3 dominant strains have good potential. It is required to further verify the passage stability so as to provide basis for industrial production.

(4) Passage Stability Experiment

The above three strains were continuously subjected to passage culture on slopes for 10 generations, and each generation of slope strains were subjected to secondary fermentation in a shake flask. Results are shown in Table 5 below.

TABLE 5

Results of passage stability of dominant strains

| | Strain number | | | | | | | |
|---|---|---|---|---|---|---|---|---|
| | HZMRYB-5 | | | HZMRYB-13 | | | HZMRYB-33 | | |
| | Titer µg/mL | Decrease rate % | A3:A4 | Titer µg/mL | Decrease rate % | A3:A4 | Titer µg/mL | Decrease rate % | A3:A4 |
| Generation 0 | 5207.67 | — | 1:5.67 | 4628.24 | — | 1:2.65 | 4861.38 | — | 1:3.90 |
| Generation 1 | 5205.24 | 0.02 | 1:5.62 | 4610.43 | 0.60 | 1:2.57 | 4518.98 | 2.70 | 1:3.42 |
| Generation 2 | 5221.15 | −0.28 | 1:5.48 | 4625.04 | 0.28 | 1:2.42 | 4325.41 | 6.86 | 1:2.68 |
| Generation 3 | 5198.43 | 0.15 | 1:5.64 | 4208.27 | 9.27 | 1:2.38 | 4008.32 | 13.69 | 1:1.74 |
| Generation 4 | 5205.58 | 0.02 | 1:5.52 | 4200.06 | 9.45 | 1:1.88 | 3860.57 | 16.87 | 1:1.52 |
| Generation 5 | 5185.87 | 0.40 | 1:5.38 | 4068.25 | 12.29 | 1:1.46 | 3852.19 | 17.05 | 1:1.20 |
| Generation 6 | 5163.79 | 0.82 | 1:5.40 | 4038.10 | 12.94 | 1:1.09 | 3744.25 | 19.38 | 1:1.12 |
| Generation 7 | 5165.44 | 0.79 | 1:5.64 | 3986.80 | 14.04 | 1:1.22 | 3764.39 | 18.94 | 1:1.09 |
| Generation 8 | 5142.37 | 1.23 | 1:5.27 | 3810.68 | 17.84 | 1:0.92 | 3648.78 | 21.43 | 1:1.13 |
| Generation 9 | 5138.25 | 1.31 | 1:5.42 | 3654.98 | 21.20 | 1:0.89 | 3621.58 | 22.02 | 1:0.97 |
| Generation 10 | 5140.68 | 1.26 | 1:5.58 | 3629.66 | 21.74 | 1:0.87 | 3548.24 | 23.60 | 1:0.86 |

As can be seen from the results, the titer of the strain HZMRYB-5 after passage for 10 generations is not obviously changed, the titer of the strain HZMRYB-13 is decreased after passage for 3 generations, and the titer of the strain HZMRYB-33 is decreased after passage for 2 generations, indicating that the strain HZMRYB-5 has good passage stability and is suitable for use as a potential industrial strain. A fermentation formulation of the strain is further optimized so as to further improve the fermentation level of the strain. In addition, the strain HZMRYB-5 is named as *Streptomyces hygroscopicus* var. *aureolacrimosus* HZMRYB-5, and has been deposited under the Budapest Treaty in China Center for Type Culture Collection (CCTCC) on Aug. 25, 2023 in Wuhan University, Wuhan, China, with a zip code of 430072 and a deposit number of CCTCC: M 20231540.

Example 2 Optimization of a Fermentation Culture Medium for the Strain HZMRYB-5

1. Culture Media

A solid (slope) culture medium, including (w/v): 0.4% of sucrose, 0.3% of skim milk powder, 0.2% of yeast powder, 0.5% of malt extract powder, 0.05% of magnesium sulfate, 0.001% of copper sulfate, 0.001% of cobalt sulfate and 2% of agar, and has a pH value of 7.2.

A seed culture medium, including (w/v): 1% of sucrose, 0.5% of skim milk powder, 0.5% of yeast extract powder, 0.5% of peptone, 0.2% of dipotassium hydrogen phosphate and the balance of water, and has a pH value of 7.2.

Fermentation culture media (w/v) are as follows.

A formulation 1, including: 10% of sucrose, 2% of skim milk powder, 2% of soybean meal powder, 2% of cottonseed cake meal, 0.1% of potassium nitrate, 0.2% of dipotassium hydrogen phosphate, 0.4% of zeolite powder, 0.005% of sodium molybdate, 0.05% of magnesium sulfate heptahydrate, 0.01% of ferrous sulfate, 0.04% of sodium acetate and the balance of water, and has a pH value of 7.2.

A formulation 2, including: 20% of sucrose, 2% of skim milk powder, 2% of soybean meal powder, 2% of cottonseed cake meal, 0.1% of potassium nitrate, 0.2% of dipotassium hydrogen phosphate, 0.4% of zeolite powder, 0.005% of sodium molybdate, 0.05% of magnesium sulfate heptahydrate, 0.01% of ferrous sulfate, 0.04% of sodium acetate and the balance of water, and has a pH value of 7.2.

A formulation 3, including: 30% of sucrose, 2% of skim milk powder, 2% of soybean meal powder, 2% of cottonseed cake meal, 0.1% of potassium nitrate, 0.2% of dipotassium hydrogen phosphate, 0.4% of zeolite powder, 0.005% of sodium molybdate, 0.05% of magnesium sulfate heptahydrate, 0.01% of ferrous sulfate, 0.04% of sodium acetate and the balance of water, and has a pH value of 7.2.

A formulation 4 including: 20% of sucrose, 2% of skim milk powder, 2% of soybean meal powder, 2% of cottonseed cake meal, 0.1% of potassium nitrate, 0.2% of dipotassium hydrogen phosphate, 0.4% of zeolite powder, 0.005% of sodium molybdate, 0.05% of magnesium sulfate heptahydrate, 0.01% of ferrous sulfate, 0.04% of sodium acetate, 0.1% of methyl oleate and the balance of water, and has a pH value of 7.2.

A formulation 5 including: 20% of sucrose, 2% of skim milk powder, 2% of soybean meal powder, 2% of cottonseed cake meal, 0.1% of potassium nitrate, 0.2% of dipotassium hydrogen phosphate, 0.4% of zeolite powder, 0.005% of sodium molybdate, 0.05% of magnesium sulfate heptahydrate, 0.01% of ferrous sulfate, 0.04% of sodium acetate, 0.5% of n-hexadecane and the balance of water, and has a pH value of 7.2.

A formulation 6 including: 20% of sucrose, 2% of skim milk powder, 2% of soybean meal powder, 2% of cottonseed cake meal, 0.1% of potassium nitrate, 0.2% of dipotassium hydrogen phosphate, 0.4% of zeolite powder, 0.005% of sodium molybdate, 0.05% of magnesium sulfate heptahydrate, 0.01% of ferrous sulfate, 0.04% of sodium acetate, 0.5% of liquid paraffin and the balance of water, and has a pH value of 7.2.

A formulation 7 including: 20% of sucrose, 2% of skim milk powder, 2% of soybean meal powder, 2% of cottonseed cake meal, 0.1% of potassium nitrate, 0.2% of dipotassium hydrogen phosphate, 0.4% of zeolite powder, 0.005% of sodium molybdate, 0.05% of magnesium sulfate heptahydrate, 0.01% of ferrous sulfate, 0.04% of sodium acetate, 0.1% of methyl oleate, 0.5% of liquid paraffin and the balance of water, and has a pH value of 7.2.

2. Fermentation Method

The high-yield strain HZMRYB-5 was subjected to passage culture on a 60 mL/250 mL eggplant-shaped flask as a slope culture medium for 15 days for later use. 1 cm$^2$ seeds on a slope were scraped off with a sterile inoculation needle, inoculated into a seed culture medium flask at a liquid loading amount of 30 mL/250 mL, and then cultured at 250 rpm at 28° C. for about 48 h to obtain a thick seed liquid. When a large amount of mycelia in a dense reticular shape were observed under a microscope, the seed liquid was transferred into a fermentation culture medium.

The seed liquid was separately inoculated into the above 7 fermentation culture medium flasks at a liquid loading amount of 30 mL/250 mL, an inoculation amount of 10% and a shaker rotation speed of 250 rpm, and then cultured at a temperature of 29° C. for a period of 13 days. During normal growth, the color of a fermentation liquid was gradually changed from gray to green and then changed from green to black. The color changed into black indicates normal metabolism of the strain. Meanwhile, mycelia were thick, reticular, deeply stained and free of hybrid bacteria in microscopic examination.

3. Titer Results

After fermentation was completed, the titer of milbemycin in a fermentation liquid was determined. Results are shown in Table 6 below.

peptone and 0.2% of dipotassium hydrogen phosphate, and has a pH value of 7.2.

A fermentation culture medium includes: 20% of sucrose, 2% of skim milk powder, 2% of soybean meal powder, 2% of cottonseed cake meal, 0.1% of potassium nitrate, 0.2% of dipotassium hydrogen phosphate, 0.4% of zeolite powder, 0.005% of sodium molybdate, 0.05% of magnesium sulfate heptahydrate, 0.01% of ferrous sulfate, 0.04% of sodium acetate, 0.1% of methyl oleate, 0.5% of liquid paraffin and the balance of water, and has a pH value of 7.2.

2. Fermentation Process: Secondary Fermentation is adopted.

(1) Culture in a Seeding Tank:

A seeding tank culture medium was prepared according to the seed culture medium (the volume after digestion was 30 L/50 L seeding tank).

The inoculation amount was maintained at a 60 mL/250 mL eggplant-shaped flask slope/30 L seed liquid; the culture temperature was 29.0° C.; the tank pressure was 0.05 MPa; the air flow was 1:1.5 vvm; the stirring rotation speed was 200 rpm; the pH was natural (7.0 before digestion and about 6.5 after digestion); and the dissolved oxygen (DO) value was controlled to be equal to or greater than 50%.

Removal indexes were as follows: At about 48 h, the pH value was 7.5, and mycelia were uniformly distributed in a reticular shape in microscopic examination.

(2) Culture in a Fermentation Tank:

A fermentation tank culture medium was prepared according to the formulation of the fermentation culture medium (the volume after digestion was 130 L/200 L fermentation tank); the inoculation amount was 10%; the culture tem-

TABLE 6

Results of the titer of milbemycin in different formulations

| | Formulation number | | | | | | |
|---|---|---|---|---|---|---|---|
| | Formulation 1 | Formulation 2 | Formulation 3 | Formulation 4 | Formulation 5 | Formulation 6 | Formulation 7 |
| Titer µg/mL | 4694.21 | 5214.79 | 5322.67 | 6072.54 | 6164.62 | 6385.43 | 6754.46 |
| A3:A4 | 1:7.26 | 1:5.48 | 1:3.85 | 1:7.02 | 1:4.86 | 1:3.43 | 1:4.36 |

As can be seen from the above results, compared with the formulations 1, 2 and 3, the fermentation titer is the highest when the sucrose concentration is 30%, but the titer is not greatly different with that when the sucrose concentration is 20%. Therefore, the optimal sucrose concentration is 20% after comprehensive consideration, and subsequent optimization is carried out on the basis of the formulation 2. On the basis of the formulation 2, the titer can be increased by 16.45% when 0.1% of methyl oleate is added, the fermentation titer of milbemycin is increased by 18.21% when 0.5% of n-hexadecane is added, the fermentation titer is increased by 22.45% when 0.5% of liquid paraffin is added, and the fermentation titer is increased by 29.53% when 0.5% of liquid paraffin and 0.1% methyl oleate are added. Therefore, the formulation 7 is determined as an optimal formulation after comprehensive consideration.

Example 3 Pilot Scale Test in a Fermentation Tank

1. Culture Media

A seed culture medium includes: 1% of sucrose, 0.5% of skim milk powder, 0.5% of yeast extract powder, 0.5% of perature was 29.0° C. in the whole process; the tank pressure was 0.05 Mpa; ventilation was controlled at 0.6 vvm at 0-24 h, gradually increased to 1.6 vvm, and then gradually decreased to 1.2 vvm before completion of fermentation; the rotation speed was gradually increased to 300 rpm at 0-48 h, and gradually decreased to 150 rpm in a later stage (from 288 h) of fermentation; the pH was natural; and the DO value was controlled to be equal to or greater than 50%.

The fermentation volume was maintained. A small amount of sterile water was supplemented every day to maintain a fermentation liquid at a constant volume.

The fermentation period was 312 h, the titer was determined at 72 h, and the titer was determined one every 24 h.

The titer of milbemycin was determined by high performance liquid chromatography (HPLC), and meanwhile, parameters, such as the pH value, the bacterial concentration and the total sugar, were detected. Results are shown in Table 7 below.

TABLE 7

Determination results of process parameters of a pilot scale test of a high-yield strain HZMRYB-5 in a fermentation tank

| Time | pH | Bacterial concentration % | Total sugar % | Stirring rpm | Air flow vvm | Dissolved oxygen % | Titer μg/mL | A3:A4 |
|---|---|---|---|---|---|---|---|---|
| 0 | 6.68 | 15 | 22.52 | 150 | 0.6 | 100 | | |
| 12 | 7.01 | 40 | 21.14 | 150 | 0.6 | 100 | | |
| 24 | 7.02 | 53 | 19.42 | 200 | 0.6 | 85 | | |
| 36 | 6.55 | 44 | 17.05 | 250 | 0.8 | 50 | | |
| 48 | 7.18 | 42 | 15.21 | 300 | 1.0 | 53 | | |
| 60 | 6.05 | 42 | 13.64 | 300 | 1.2 | 50 | | |
| 72 | 7.01 | 42 | 12.78 | 300 | 1.4 | 50 | 993.03 | 1:0.63 |
| 84 | 7.01 | 42 | 11.68 | 300 | 1.6 | 65 | | |
| 96 | 7.00 | 42 | 10.52 | 300 | 1.6 | 64 | 1596.99 | 1:0.85 |
| 108 | 7.00 | 42 | 9.46 | 300 | 1.6 | 64 | | |
| 120 | 7.00 | 42 | 8.41 | 300 | 1.6 | 72 | 2209.95 | 1:0.98 |
| 132 | 7.00 | 42 | 9.40 | 300 | 1.6 | 74 | | |
| 144 | 6.99 | 42 | 8.39 | 300 | 1.6 | 75 | 2849.98 | 1:1.36 |
| 156 | 6.98 | 42 | 7.36 | 300 | 1.6 | 77 | | |
| 168 | 6.99 | 42 | 6.41 | 300 | 1.6 | 76 | 3356.49 | 1:1.89 |
| 180 | 6.99 | 42 | 5.25 | 300 | 1.6 | 74 | | |
| 192 | 6.99 | 42 | 4.44 | 300 | 1.6 | 75 | 3971.47 | 1:3.15 |
| 204 | 6.99 | 42 | 3.68 | 300 | 1.6 | 77 | | |
| 216 | 6.99 | 42 | 2.78 | 300 | 1.6 | 76 | 4457.14 | 1:4.08 |
| 228 | 7.03 | 42 | 1.98 | 300 | 1.6 | 74 | | |
| 240 | 7.06 | 42 | 1.09 | 300 | 1.6 | 75 | 5062.47 | 1:5.15 |
| 252 | 7.08 | 42 | 0.81 | 300 | 1.4 | 76 | | |
| 264 | 7.10 | 42 | 0.65 | 200 | 1.4 | 75 | 5686.77 | 1:5.29 |
| 276 | 7.15 | 42 | 0.48 | 200 | 1.4 | 74 | | |
| 288 | 7.27 | 41 | 0.32 | 150 | 1.2 | 76 | 5937.99 | 1:6.04 |
| 300 | 7.30 | 41 | 0.30 | 150 | 1.2 | 75 | | |
| 312 | 7.31 | 41 | 0.29 | 150 | 1.2 | 74 | 6003.47 | 1:6.09 |

As can be seen from the above results, the titer is slowly increased after fermentation is carried out for 264 h, mycelia are melted, the pH value of the fermentation liquid is increased, and the fermentation process is in a late stage. Meanwhile, as can be seen from the pilot scale test results and process parameters, the increase trend of the titer in a middle fermentation stage is relatively good, and at this time, little amounts of carbon sources, nitrogen sources, trace elements and the like can be added to prolong the increase period of the titer, so as to further improve the fermentation level.

Example 4 High-Density Fermentation Process of Supplements

1. Culture Media

A seed culture medium includes: 1% of sucrose, 0.5% of skim milk powder, 0.5% of yeast extract powder, 0.5% of peptone and 0.2% of dipotassium hydrogen phosphate, and has a pH value of 7.2.

A fermentation culture medium includes: 20% of sucrose, 2% of skim milk powder, 2% of soybean meal powder, 2% of cottonseed cake meal, 0.1% of potassium nitrate, 0.2% of dipotassium hydrogen phosphate, 0.4% of zeolite powder, 0.005% of sodium molybdate, 0.05% of magnesium sulfate heptahydrate, 0.01% of ferrous sulfate, 0.04% of sodium acetate, 0.1% of methyl oleate, 0.5% of liquid paraffin and the balance of water, and has a pH value of 7.2.

A supplement culture medium includes: all materials in the formulation of the fermentation culture medium with a double concentration.

2. Fermentation Process: Secondary fermentation is adopted.

(1) Culture in a Seeding Tank:

A seeding tank culture medium was prepared according to the formulation of the seed culture medium (the volume after digestion was 30 L/50 L seeding tank).

The inoculation amount was maintained at a 60 mL/250 mL eggplant-shaped flask slope/30 L seed liquid; the culture temperature was 29.0° C.; the tank pressure was 0.05 MPa; the air flow was 1:1.5 vvm; the stirring rotation speed was 200 rpm; the pH was natural (7.0 before digestion and about 6.5 after digestion); and the dissolved oxygen (DO) value was controlled to be equal to or greater than 50%.

Removal indexes were as follows: At about 48 h, the pH value was 7.5, and mycelia were uniformly distributed in a reticular shape in microscopic examination.

(2) Culture in a Fermentation Tank:

A fermentation tank culture medium was prepared according to the formulation of the fermentation culture medium (the volume after digestion was 130 L/200 L fermentation tank); the inoculation amount was 10%; the temperature was 29.0° C. in the whole process; the tank pressure was 0.05 Mpa; ventilation was controlled at 0.6 vvm at 0-24 h, gradually increased to 1.6 vvm, and then gradually decreased to 1.2 vvm before completion of fermentation; the rotation speed was gradually increased to 300 rpm at 0-48 h, the stirring rotation speed was decreased in a later stage of fermentation, and the rotation speed was gradually decreased to 150 rpm before completion of fermentation; the pH was natural (No additional acid or base is needed to adjust the pH of the system); and the DO value was controlled to be equal to or greater than 50%.

The fermentation volume was maintained. A small amount of sterile water was supplemented every day according to the volume of a fermentation liquid to maintain the fermentation liquid at a constant volume.

The fermentation period was 384 h, the titer was determined at 72 h, and the titer was determined one every 24 h.

At about 192 h, when the total sugar content was about 6.0%, the supplement culture medium was supplemented in three times every day according to 3% of the volume of the fermentation liquid.

The titer of milbemycin was determined by HPLC, and meanwhile, parameters, such as the pH value, the bacterial concentration and the total sugar, were detected. Results are shown in Table 8 below.

TABLE 8

Determination results of parameters of a high-density fermentation process of supplements

| Time | pH | Bacterial concentration % | Total sugar % | Stirring rpm | Air flow vvm | Dissolved oxygen % | Titer μg/mL | A3:A4 |
|---|---|---|---|---|---|---|---|---|
| 0 | 6.69 | 14 | 21.47 | 150 | 0.6 | 100 | | |
| 12 | 7.02 | 39 | 21.22 | 150 | 0.6 | 100 | | |
| 24 | 7.01 | 51 | 19.87 | 200 | 0.6 | 85 | | |
| 36 | 6.53 | 41 | 17.43 | 250 | 0.8 | 50 | | |
| 48 | 7.21 | 41 | 15.36 | 300 | 1.6 | 53 | | |
| 60 | 6.01 | 41 | 13.52 | 300 | 1.6 | 50 | | |
| 72 | 7.01 | 42 | 12.96 | 300 | 1.6 | 50 | 943.39 | 1:0.58 |
| 84 | 7.01 | 42 | 11.52 | 300 | 1.6 | 65 | | |
| 96 | 7.01 | 42 | 10.44 | 300 | 1.6 | 64 | 1513.91 | 1:0.81 |
| 108 | 7.01 | 42 | 9.32 | 300 | 1.6 | 64 | | |
| 120 | 7.02 | 42 | 8.25 | 300 | 1.6 | 72 | 2096.88 | 1:0.93 |
| 132 | 7.02 | 42 | 9.31 | 300 | 1.6 | 74 | | |
| 144 | 7.02 | 42 | 8.46 | 300 | 1.6 | 75 | 2712.36 | 1:1.42 |
| 156 | 7.02 | 42 | 7.38 | 300 | 1.6 | 77 | | |
| 168 | 7.02 | 42 | 6.32 | 300 | 1.6 | 79 | 3318.11 | 1:1.86 |
| 180 | 6.96 | 42 | 6.09 | 300 | 1.6 | 74 | | |
| 192 | 6.96 | 43 | 6.04 | 300 | 1.6 | 75 | 3880.32 | 1:3.21 |
| 204 | 6.96 | 45 | 5.52 | 300 | 1.6 | 77 | | |
| 216 | 6.96 | 46 | 5.74 | 300 | 1.6 | 79 | 4435.37 | 1:4.16 |
| 228 | 6.96 | 47 | 5.89 | 300 | 1.6 | 74 | | |
| 240 | 6.98 | 47 | 6.18 | 300 | 1.6 | 75 | 4980.38 | 1:4.93 |
| 252 | 6.98 | 47 | 5.83 | 300 | 1.4 | 73 | | |
| 264 | 6.98 | 47 | 5.56 | 200 | 1.4 | 72 | 5537.64 | 1:5.12 |
| 276 | 6.98 | 47 | 5.48 | 200 | 1.4 | 74 | | |
| 288 | 6.98 | 47 | 5.32 | 200 | 1.4 | 76 | 6038.37 | 1:5.36 |
| 300 | 6.99 | 47 | 5.05 | 200 | 1.4 | 72 | | |
| 312 | 6.99 | 46 | 4.36 | 200 | 1.4 | 73 | 6450.75 | 1:5.67 |
| 324 | 6.99 | 46 | 3.85 | 200 | 1.4 | 75 | | |
| 336 | 7.00 | 46 | 3.18 | 200 | 1.4 | 74 | 6627.65 | 1:5.89 |
| 348 | 7.06 | 46 | 2.43 | 200 | 1.4 | 73 | | |
| 360 | 7.17 | 46 | 2.01 | 150 | 1.2 | 70 | 6974.17 | 1:6.08 |
| 372 | 7.26 | 46 | 1.58 | 150 | 1.2 | 70 | | |
| 384 | 7.32 | 46 | 0.96 | 150 | 1.2 | 70 | 7069.85 | 1:6.27 |

As can be seen from the above results, the fermentation time can be prolonged to 384 h after fermentation of supplements, and the titer of milbemycin can reach 7069.85 μg/mL at this time, which is improved by 17.76% compared with that before adding supplements, indicating that the fermentation time can be prolonged by adding supplements, and the fermentation titer of the milbemycin strain HZM-RYB-5 can be obviously improved.

Example 5 Fermentation Process of Mixed Strains

1. Strains: MI-W1-2017001 (A3:A4=1:0.78) and HZMRYB-5 (A3:A4=1:5.67) were used.
2. Culture Media A seed culture medium includes: 1% of sucrose, 0.5% of skim milk powder, 0.5% of yeast extract powder, 0.5% of peptone and 0.2% of dipotassium hydrogen phosphate, and has a pH value of 7.2.

A fermentation culture medium includes: 20% of sucrose, 2% of skim milk powder, 2% of soybean meal powder, 2% of cottonseed cake meal, 0.1% of potassium nitrate, 0.2% of dipotassium hydrogen phosphate, 0.4% of zeolite powder, 0.005% of sodium molybdate, 0.05% of magnesium sulfate heptahydrate, 0.01% of ferrous sulfate, 0.04% of sodium acetate, 0.1% of methyl oleate, 0.5% of liquid paraffin and the balance of water, and has a pH value of 7.2.

A supplement culture medium includes: all materials in the formulation of the fermentation culture medium with a double concentration.

3. Fermentation Process: Secondary fermentation is adopted.

(1) Culture in a Seeding Tank:

Four seeding tanks were prepared according to the formulation of the seed culture medium (the volume after digestion was 30 L/50 L seeding tank); spore suspensions containing MI-W1-2017001 and HZMRYB-5 at different ratios were sequentially inoculated (according to the ratios shown in Table 9), and the inoculation amount was maintained at a seed amount on a 60 mL/250 mL eggplant-shaped flask slope/30 L seed liquid; the culture temperature was 29.0° C.; the tank pressure was 0.05 MPa; the air flow was 1:1.5 vvm; the stirring rotation speed was 200 rpm; the pH was natural (7.0 before digestion and about 6.5 after digestion); and the DO value was controlled to be equal to or greater than 50%.

Removal indexes were as follows: At about 48 h, the pH value was 7.5, and mycelia were uniformly distributed in a reticular shape in microscopic examination.

(2) Culture in a Fermentation Tank:

Four fermentation tank culture media were prepared according to the fermentation culture medium (the volume after digestion was 130 L/200 L fermentation tank); seed liquids prepared in step (1) were inoculated at an amount of 10%, respectively; the culture temperature was 29.0° C. in the whole process; the tank pressure was 0.05 Mpa; ventilation was controlled at 0.6 vvm at 0-24 h, gradually increased to 1.6 vvm, and then gradually decreased to 1.2 vvm before completion of fermentation; the rotation speed was gradually increased to 300 rpm at 0-48 h, and then gradually decreased to 150 rpm before completion of fermentation; the pH was natural; and the DO value was controlled to be equal to or greater than 50% (specific time for adjusting the ventilation and the rotation speed refers to Table 8).

The fermentation volume was maintained. A small amount of sterile water was supplemented every day according to the volume of a fermentation liquid to maintain the fermentation liquid at a constant volume.

At about 180 h, when the total sugar content was about 6.0%, the supplement culture medium was supplemented in three times every day according to 3% of the volume of the fermentation liquid.

The whole fermentation period was 384 h, the titer was determined at 72 h, and the titer was determined one every 24 h. Results are shown in Table 9 below.

TABLE 9

Results of mixed fermentation of strains MI-W1-2017001 and HZMRYB-5 at different ratios

| Fermentation time h | Ratio of strains MI-W1-2017001 and HZMRYB-5 | | | | | | | |
|---|---|---|---|---|---|---|---|---|
| | 1:0.5 | | 1:1 | | 1:2 | | 1:3 | |
| | Titer | A3:A4 | Titer | A3:A4 | Titer | A3:A4 | Titer | A3:A4 |
| 72 | 891.04 | 1:0.58 | 903.25 | 1:0.53 | 892.50 | 1:0.57 | 860.42 | 1:0.60 |
| 96 | 1478.55 | 1:0.83 | 1498.65 | 1:0.78 | 1476.59 | 1:0.76 | 1437.19 | 1:0.71 |
| 120 | 1860.49 | 1:1.30 | 1958.47 | 1:1.10 | 1903.20 | 1:0.92 | 1863.25 | 1:0.84 |
| 144 | 2478.52 | 1:1.76 | 2600.14 | 1:1.26 | 2589.66 | 1:1.04 | 2537.18 | 1:0.93 |
| 168 | 3015.63 | 1:2.01 | 3088.16 | 1:1.40 | 3053.24 | 1:1.15 | 3006.46 | 1:1.02 |
| 192 | 3568.24 | 1:2.21 | 3598.14 | 1:1.65 | 3579.32 | 1:1.23 | 3542.85 | 1:1.12 |
| 216 | 4013.25 | 1:2.43 | 4055.42 | 1:1.92 | 4025.38 | 1:1.39 | 4008.23 | 1:1.28 |
| 240 | 4588.96 | 1:2.65 | 4608.24 | 1:2.09 | 4556.21 | 1:1.54 | 4507.39 | 1:1.40 |
| 264 | 4985.12 | 1:2.84 | 5047.85 | 1:2.23 | 4968.54 | 1:1.63 | 4987.12 | 1:1.51 |
| 288 | 5398.66 | 1:3.06 | 5415.40 | 1:2.47 | 5398.76 | 1:1.74 | 5358.71 | 1:1.65 |
| 312 | 5907.42 | 1:3.25 | 5923.47 | 1:2.63 | 5900.20 | 1:1.95 | 5814.69 | 1:1.76 |
| 336 | 6219.48 | 1:3.69 | 6305.18 | 1:2.89 | 6298.47 | 1:2.08 | 6278.43 | 1:1.85 |
| 360 | 6477.53 | 1:4.02 | 6522.38 | 1:3.04 | 6472.53 | 1:2.21 | 6542.38 | 1:1.96 |
| 384 | 6850.42 | 1:4.25 | 6907.43 | 1:3.16 | 6886.24 | 1:2.35 | 6720.15 | 1:2.03 |

As can be seen from the results of a mixed fermentation test, after the strains MI-W1-2017001 and HZMRYB-5 are mixed at a ratio of 1:2, the ratio of A3 and A4 in a later stage of fermentation is 3:7.05 (1:2.35), which basically meets the requirement for 3:7. Therefore, milbemycin meeting the requirement for the ratio of A3 and A4 can be produced by fermentation of mixed strains.

Although the present invention has been disclosed as better embodiments, the embodiments are not intended to limit the present invention. For any person skilled in the art, changes, modifications, substitutions and alternations of the embodiments in various forms and details can be made without deviating from the spirit and principles of the present invention. The scope of the present invention is limited by the claims and equivalents thereof.

What is claimed is:

1. A strain of *Streptomyces hygroscopicus* var. *aureolacrimosus*, wherein the strain is a mutant of the *Streptomyces hygroscopicus* var. *aureolacrimosus*, the strain is *Streptomyces hygroscopicus* var. *aureolacrimosus* HZMRYB-5, with a deposit number of CCTCC: M 20231540.

2. A method for producing milbemycin by the strain of *Streptomyces hygroscopicus* var. *aureolacrimosus* HZMRYB-5 of claim 1, comprising taking the strain of *Streptomyces hygroscopicus* var. *aureolacrimosus* HZMRYB-5 of claim 1 to perform fermentation.

3. A method for producing milbemycin by fermentation of *Streptomyces hygroscopicus* var. *aureolacrimosus* HZMRYB-5, specifically comprising: inoculating a seed liquid of a strain HZMRYB-5 into a fermentation culture medium at an inoculation amount of 5-20% by volume fraction, wherein the strain HZMRYB-5 is *Streptomyces hygroscopicus* var. *aureolacrimosus* HZMRYB-5 with a deposit number of CCTCC: M 20231540, the culture temperature is 28.0-30.0° C. during whole fermentation process;

the tank pressure is 0.02-0.06 MPa; ventilation is controlled at 0.2-1.0 vvm at 0-24 h, gradually increased to 1.0-1.8 vvm, and then gradually decreased to 1.0-1.2 vvm before completion of fermentation; the rotation speed is gradually increased to 250-500 rpm at 0-48 h, and gradually decreased to 100-200 rpm in a later stage of fermentation; natural pH; the dissolved oxygen (DO) value is controlled to be equal to or greater than 50%; and the fermentation period is 300-400 h;

when the total sugar content is 5.0-8.0%, a supplement culture medium is supplemented in 1-3 times every day according to 1-4% of the volume of the fermentation liquid;

wherein the supplement culture medium comprises: all materials in the formulation of the fermentation culture medium with a double concentration;

and a w/v composition of the fermentation culture medium is: 10-30% of sucrose, 0.5-3% of skim milk powder, 2-4% of soybean meal powder, 1-4% of cottonseed cake meal, 0.1-0.5% of potassium nitrate, 0.1-0.5% of dipotassium hydrogen phosphate, 0.1-1.0% of zeolite powder, 0.001-0.01% of sodium molybdate, 0.01-0.1% of magnesium sulfate heptahydrate, 0.01-0.05% of ferrous sulfate, 0.01-0.1% of sodium acetate, 0.1-1% of methyl oleate, 0.1-1% of liquid paraffin and the balance of water, and has a pH value of 7.2.

4. The method for producing milbemycin by fermentation according to claim 3, wherein sterile water is supplemented every day to maintain a fermentation liquid at a constant volume.

5. A method for producing milbemycin by fermentation, wherein a seed liquid is obtained by mixed culture of a strain MI-W1-2017001 and a strain HZMRYB-5;
and the strain HZMRYB-5 is *Streptomyces hygroscopicus* var. *aureolacrimosus* HZMRYB-5, with a deposit number of CCTCC: M 20231540;
and the strain MI-W1-2017001 is specifically *Streptomyces hygroscopicus* var. *aureolacrimosus* MI-W1-2017001, with a deposit number of CCTCC NO: M 2021292;
wherein the seed liquid is inoculated into a fermentation culture medium at an inoculation amount of 5-20%; the culture temperature is 28.0-30.0° C. in the whole process; the tank pressure is 0.02-0.06 Mpa; ventilation is controlled at 0.2-1.0 vvm at 0-24 h, gradually increased to 1.0-1.8 vvm, and then gradually decreased to 1.0-1.2 vvm at 12-144 h before completion of fermentation; the rotation speed is gradually increased to 250-500 rpm at 0-48 h, and gradually decreased to 100-200 rpm at 20-120 h before completion of fermentation; natural pH; the DO value is controlled to be equal to or greater than 50%; and the fermentation period is 300-400 h;
when the total sugar content is about 5.0-8.0%, a supplement culture medium is supplemented in 1-3 times every day according to 1-4% of the volume of the fermentation liquid; the supplement culture medium comprises: all materials in a formulation of the fermentation culture medium with a double concentration;
a w/v composition of the fermentation culture medium is: 20% of sucrose, 2% of skim milk powder, 2% of soybean meal powder, 2% of cottonseed cake meal, 0.1% of potassium nitrate, 0.2% of dipotassium hydrogen phosphate, 0.4% of zeolite powder, 0.005% of sodium molybdate, 0.05% of magnesium sulfate heptahydrate, 0.01% of ferrous sulfate, 0.04% of sodium acetate, 0.1% of methyl oleate, 0.5% of liquid paraffin and the balance of water, and has a pH value of 7.2;
and the seed liquid is obtained by mixed culture of a strain MI-W1-2017001 and a strain HZMRYB-5, and during preparation of the seed liquid, the strain MI-W1-2017001 and the strain HZMRYB-5 are inoculated at a ratio of 1:2.

\* \* \* \* \*